Figure 1:
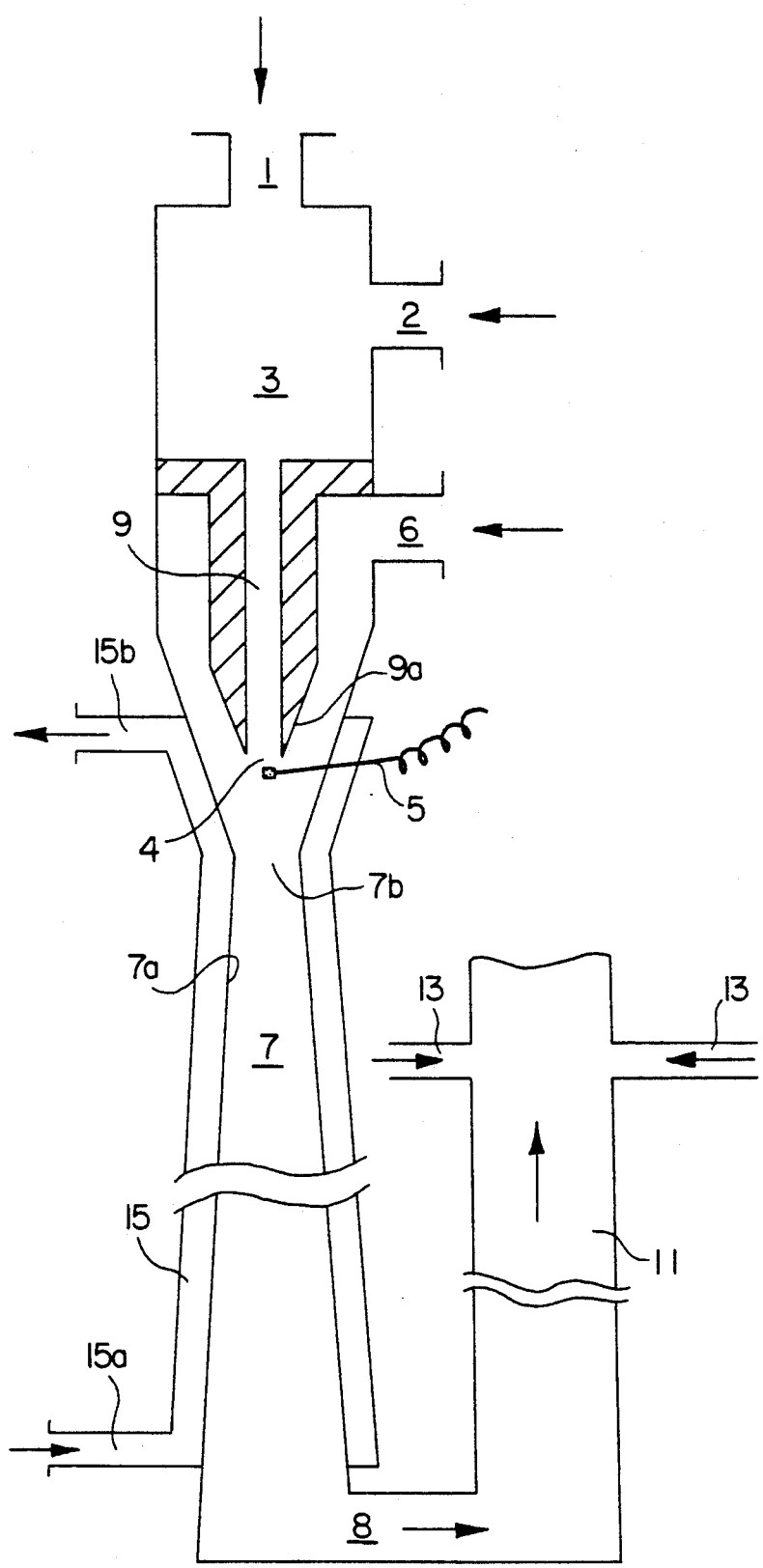

United States Patent [19]

Côme

[11] Patent Number: 5,268,525
[45] Date of Patent: * Dec. 7, 1993

[54] PROCESS AND APPARATUS FOR CONVERTING SATURATED HYDROCARBONS

[75] Inventor: Guy-Marie Côme, Nancy, France

[73] Assignee: Gaz de France, Paris, France

[*] Notice: The portion of the term of this patent subsequent to Aug. 28, 2007 has been disclaimed.

[21] Appl. No.: 670,583

[22] Filed: Mar. 18, 1991

[30] Foreign Application Priority Data

Mar. 27, 1990 [FR] France ............... 90 04150

[51] Int. Cl.$^5$ ............................... C07C 2/00
[52] U.S. Cl. ..................... 585/500; 585/612; 585/654; 585/656; 585/657
[58] Field of Search ........... 585/500, 612, 654, 656, 585/657

[56] References Cited

U.S. PATENT DOCUMENTS

| | | | |
|---|---|---|---|
| 2,143,014 | 1/1939 | Klein | 585/656 |
| 3,306,950 | 2/1967 | Bajars | 585/657 |
| 3,308,197 | 3/1967 | Bajars | 585/657 |
| 4,199,533 | 4/1980 | Benson | 585/657 |
| 4,634,800 | 1/1987 | Withers, Jr. et al. | 585/656 |
| 4,952,743 | 8/1990 | Come | 585/540 |
| 4,973,786 | 11/1990 | Karra | 585/656 |

Primary Examiner—Patrick P. Garvin
Assistant Examiner—E. D. Irzinski
Attorney, Agent, or Firm—Pollock, Vande Sande & Priddy

[57] ABSTRACT

The invention relates to the conversion of saturated hydrocarbons.

According to the invention a first gas containing chlorine and a second gas containing hydrogen are introduced into a chamber (3) so as to mix them. At the exit (4) of this chamber (3) the mixture of chlorine and hydrogen is ignited and the products originating from this flame are then mixed in a chamber (7) with a third gas containing the hydrocarbons to be converted, with a mean weight content of hydrogen element of at least 18%. The effluents from the chamber (7) are collected, quenched and fractionated. The hydrochloric acid is reformed into chlorine which is recycled in the first gas, the hydrogen is recycled in the second gas, and the alkanes in the third gas. The unsaturated hydrocarbons are recovered.

The invention applies in particular to the conversion of natural gases into unsaturated hydrocarbons, such as ethylene.

15 Claims, 2 Drawing Sheets

PROCESS AND APPARATUS FOR CONVERTING SATURATED HYDROCARBONS

The present invention relates in particular to a process for converting saturated hydrocarbons, such as methane, into unsaturated hydrocarbons, such as ethylene.

The objective addressed is, advantageously, to convert hydrocarbon raw materials into base products intended particularly for chemical industries.

The hydrocarbon charges which can be singled out within the scope of the invention are characterised by a mean weight content of hydrogen element in the hydrocarbons of at least approximately 18%.

This is the case especially of methane-rich gaseous hydrocarbon raw materials such as natural gases and synthetic natural gases, and some gases produced by gasification of various carbonaceous materials such as coal, or else produced from biomass or from various wastes. It is also the case of methane, of ethane, of propane and of their mixtures in any proportions.

Butanes, light and naphtha gasolines, heavy petroleum fractions or those resulting from its refining and, more generally, liquid or gaseous hydrocarbons which have a hydrogen-element mean weight content lower than 18% can be employed within the scope of the invention as additional charges, provided that they are mixed with another hydrocarbon charge of hydrogen-element mean weight content which is sufficiently higher than 18% for the resulting charge to have a hydrogen-element mean weight content higher than approximately 18%.

The hydrocarbon raw materials employed to make up the hydrocarbon charges singled out within the scope of the invention can contain small quantities of inorganic gases and of various sulphur or oxygen compounds. The removal of these substances from the hydrocarbon charges should not be necessary within the scope of the invention.

As for the base products which are obtained by converting these raw materials, and which are at present widely employed in chemical industries, these are unsaturated hydrocarbons of low molecular weight, such as ethylene.

Various types of hydrocarbon conversion processes exist at present.

Where hydrocarbons containing at least two carbon atoms are concerned, that is to say starting with ethane, the most widespread process is steam cracking. This process cannot be applied to gases which are rich in methane.

Where these methane-rich gases are concerned, these are employed primarily as fuel, but there are also various processes for converting methane into base chemical products, such as synthesis gas or acetylene.

Methane conversion has also been obtained by homogeneous processes employing chlorine. These processes can be classified into two large categories.

Two-stage processes consist especially in first manufacturing methyl chloride by chlorinating methane at a relatively low temperature and then pyrolysing methyl chloride by itself (U.S. Pat. No. 2,320,274) or in the presence of oxygen (U.S. Pat. No. 4,714,796), especially with a view to obtaining unsaturated hydrocarbons. These processes have the disadvantage of resulting in the formation of tars and soots, even though the addition of oxygen tends to reduce this.

Single-stage processes (for example U.S. Pat. No. 4,199,233) consist in particular in reacting methane and chlorine in a flame at a relatively high temperature with a view to producing ethylene and ethane directly. These latter processes also result in the formation of tars and soots.

The objective of the invention is precisely to solve the difficulties and disadvantages of the various known processes for converting gases which may contain methane and, above all, involve the use of chlorine. This objective is attained in the invention by making provision for:

using, as starting substances, a first gas containing at least of the order of 30% by volume of chlorine, a second gas containing at least approximately 30% by volume of hydrogen, and a third gas containing at least approximately 60% by weight of a charge of one or more hydrocarbons with a mean weight content of hydrogen element of at least approximately 18%, and in a given gas circulation zone, igniting the chlorine and the hydrogen of the said first and second gases which are then in contact, while obeying a spatial distribution such that these first two gases are surrounded by the third, and mixing the inflamed substances obtained with this third gas so as to induce the hydrocarbon conversion reactions.

Insofar as the exothermic reaction between the chlorine and the hydrogen is concerned, both premixing flames and diffusion flames can be envisaged.

It will be noted, furthermore, where the hydrocarbon charge present in the third gas is concerned, that this may contain alkanes or paraffins, including methane, cyclanes, cyclanoaromatics, aromatics, or even olefins, the only condition being that the mean weight content of hydrogen element should be higher than, or of the order of, 18%.

It will also be noted, with regard to the quantities by volume of chlorine, hydrogen and of alkanes (including methane) which are introduced overall in the first, second and third gases, that a chlorine/alkanes ratio lower than or equal to 1/1 and that a hydrogen/-chlorine ratio higher than or equal to ½ are recommended.

The products leaving the reactor include alkanes which have not reacted and/or those formed during the reaction, unsaturated hydrocarbons, hydrogen and hydrochloric acid.

These various products are then separated from each other by known processes.

Hydrochloric acid is converted into chlorine by an oxidation reaction, according to the equation:

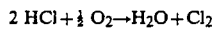

$$2\ HCl + \tfrac{1}{2}\ O_2 \rightarrow H_2O + Cl_2$$

The chlorine which is re-formed can be recycled to form the first starting gas (wholly or partially).

The hydrogen collected as a result of the fractionation can also be recycled to form, at least partially, the second starting gas.

The paraffins collected as a result of the fractionation can in their case also be recycled to form, at least partially, the third starting gas.

The unsaturated hydrocarbons originating from the fractionation section can, in their case, be collected and stored for a subsequent utilization.

In addition to the process which has just been described, another subject of the invention is a conversion apparatus or reactor which therefore permits the conversion of saturated hydrocarbons into unsaturated hydrocarbons.

According to an important characteristic of the invention, this apparatus comprises:

a reaction chamber for mixing and reacting therein a first gas containing chlorine, a second gas containing hydrogen and a third gas containing a hydrocarbon charge, means of ignition for inflaming the first and second gases and inducing the conversion reaction in the presence of the third gas, and means of recovery communicating with the reaction chamber to collect the effluents originating from this chamber and containing the said unsaturated hydrocarbons.

Thus produced, this apparatus will make it possible to implement the process described above while obtaining the same results which are advantageous when compared with traditional units of apparatus employing especially the single- or two-stage processes.

According to an advantageous additional characteristic, this apparatus may have preheating chambers for preheating at least the hydrocarbon charge to be converted, these chambers lying externally in contact with the outer wall of the reaction chamber which will then be thermally conductive, so as simultaneously to preheat this hydrocarbon charge before it is introduced into the reaction chamber and to create in the latter, a zone of internal quenching by heat transfer through the said conductive wall of this chamber.

It will be possible in this way to optimize the performance of the reactor and its construction cost.

It will be noted that in order to promote this optimisation and for practical conditions of construction of the apparatus, it may be preferable to produce the reaction chamber with a ratio of its wetted surface to its volume of between approximately 40 and 250 $m^{-1}$, advantageously with a rectangular section.

Figure 2:
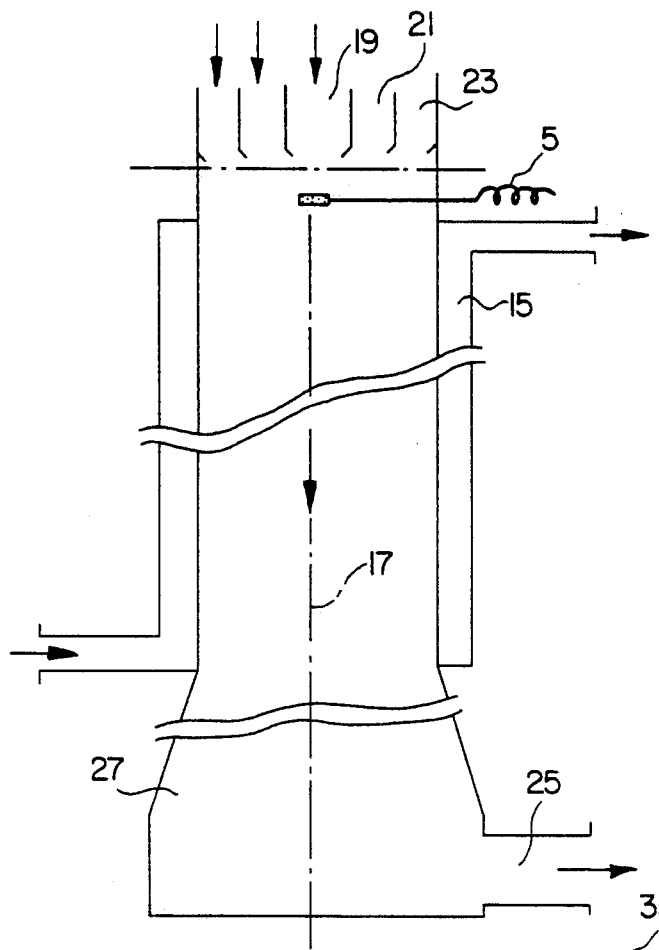
Figure 3:
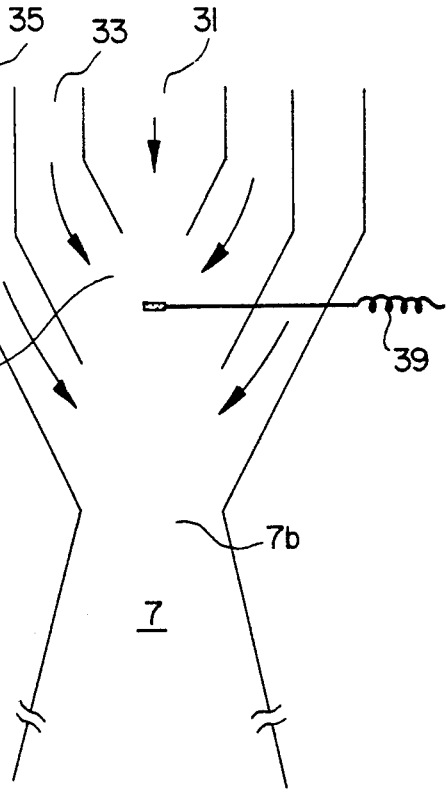

Other subjects, characteristics and advantages of the invention, will appear more clearly from the description which is to follow and which is given with reference to the attached drawings, in which:

FIG. 1 is a diagram illustrating a first embodiment of the process according to the invention, FIG. 2 is a diagram illustrating a second embodiment of the process according to the invention, and FIG. 3 is a diagram showing a local alternative form of embodiment of the apparatus shown in FIG. 2.

If reference is made first of all to FIG. 1, it can be seen that the first gas containing chlorine is introduced via the axial conduit 1, the second gas containing hydrogen being introduced via a transverse conduit 2. These two gases are premixed in a chamber 3 and ignited at the exit 4 of this chamber by an igniting device 5 which is known per se (electric arc, auxiliary flame, etc.), after having passed through the neck- or nozzle-shaped tube 9, of substantially uniform section. The third gas containing the hydrocarbon charge to be converted is introduced via the transverse conduit 6 into a chamber 7 and is mixed with the premixing flame gases originating from the orifice 4, so as to induce the hydrocarbon conversion reactions. In its upstream part, the mixing-reaction chamber 7 has a converging part, a neck, and then a long divergent downstream part. The effluents from the chamber 7 are collected by a conduit 8, to be quenched and fractionated using processes which are known per se.

After fractionation, the hydrochloric acid is converted into chlorine in an auxiliary plant by a process which is known per se, and the chlorine is recycled towards the conduit 1, the hydrogen is recycled towards the conduit 2, the alkanes are recycled towards the conduit 6, the unsaturated hydrocarbons are collected and stored for a subsequent utilization.

To avoid overloading FIG. 1, the recycle conduits have not been shown.

It has been noted that the yield of potentially valuable conversion products of the process is improved by a preheating, especially of the third gas containing the hydrocarbon charge. This preheating may be carried out by various processes, for example by heat exchange through the walls of the chamber 7 or by recovery of the latent heat of the gases originating from the conduit 8 by means of a quench fluid, or by recovery of the heat released by the oxidation of hydrochloric acid, or else by heating the hydrocarbon charge using the heat released by combustion either of a fraction of the charge itself or of an auxiliary fuel, or even by heating using low-grade electrical energy, it being understood that these means can be used separately or concurrently, wholly or partially.

Furthermore, a conventional "direct" quenching column, that is to say for quenching using injection or introduction of a quenching fluid via the conduits 13, is shown at 11, at the exit of the conduit 8. It is possible to envisage employing hydrogen or a hydrocarbon, and in particular a "light" hydrocarbon (one containing fewer than five carbon atoms) as a quenching fluid of this kind, so as to induce so-called reactive quenching.

Other types of quenching could, of course, be employed, such as quenching with a liquid injected, for example, into the bottom part of the chamber 7.

According to an important characteristic of the invention, it would also be possible to provide "indirect" quenching of the products circulating in the conversion chamber 7.

The walls 7a which define this chamber externally will then be thermally conductive. It is quite possible to conceive their being made of metal (especially of nickel, a metal which resists chlorine) or of ceramics, and this even offers appreciable advantages.

It is then possible, in particular, to link the quenching of the conversion products circulating in the chamber 7 with the preheating of all or part of the reactants, and especially of the hydrocarbon charge which then circulates (preferably countercurrentwise) in one or more preheating chambers such as 15, which lie around the chamber 7, along the latter, in contact with its outer walls 7a, to permit the heat transfer.

To obtain satisfactory results in the case of this combined and concurrent indirect quenching/preheating action, it is recommended, however, to provide a ratio of the wetted surface of the walls of the chamber 7 to the volume of this same chamber of between 40 and 250 $m^{-1}$. These limits are explained, on the one hand, by the problems of effectiveness of the heat exchanges (which are insufficient below 40 $m^{-1}$) and, on the other hand, by difficulties of industrial implementation, related in particular to the materials of construction of the chamber walls, to the minimum separation between these walls permitting the reactants to circulate, to the thickness of the burner lips 9a, etc.

Bearing in mind these requirements, a construction of this chamber 7 with a rectangular section should be preferred (in this case at the expense of a normally circular section).

For an optimum effectiveness, the entry 15a of the preheating chamber(s) 15 can be situated near the base of the conversion chamber 7, with the reactant(s) to be preheated then circulating countercurrentwise to the products contained in the reactor, to leave again at 15b in line with the upper part of this chamber 7, near its neck 7b.

The temperature of the gases inside the chamber 7 is difficult to specify and depends on the operating conditions, in particular on the possible preheating temperature of the hydrocarbon charge, on the nature of this charge, and on the proportions of chlorine and hydrogen which are used. The hydrocarbon conversion temperatures should be between 700° and 1600° C. in the upstream part of the chamber 7. By virtue of the particular spatial distribution of the various gases as they enter the chamber 7, the third gas containing the hydrocarbons to be prolyzed acts as a heat insulator between the flame issuing from the orifice 4 and the walls of the upstream part of the chamber 7, and this ensures a decrease in the thermal stresses in the reactor.

The reaction may be conducted at a pressure close to atmospheric pressure, but it may also be conducted at lower pressures, down to approximately $0.5 \times 10^5$ Pa, or higher ones, up to approximately $50 \times 10^5$ Pa The residence times of the substances in the reaction chamber 7 will be generally shorter than 1 s.

Let us now turn to FIG. 2, which illustrates an alternative form of embodiment of the invention.

In this alternative form, the reaction chamber 7, which has a substantially uniform rectangular section, is connected in its upper part to a series of reactant feed streams or conduits 19, 21, 23. Near the chamber, these various streams lie along axes which are substantially parallel to the lengthwise direction 17 of this chamber.

The central conduit 19 in this case is intended to feed the chamber 7 with chlorine or with a mixture of chlorine and hydrogen. In an extreme case the second conduit 21 could be omitted. When it is provided, this conduit is employed for feeding the chamber with hydrogen, this therefore being essential in the case where this hydrogen is not delivered either by the first (19) or by the third conduit 23, the latter being therefore used to feed the chamber 7 either with a mixture of saturated hydrocarbons to be converted and hydrogen, or with saturated hydrocarbons by themselves. Insofar as the nature of the constituents is concerned, this is still the same, it being necessary for the chamber to receive, from the centre towards the outside of the reactor, essentially chlorine, hydrogen and the hydrocarbon charge.

If three such streams are provided, a first gas containing at least 30% by volume of chlorine will therefore circulate in the first central stream 19, a second gas containing at least approximately 30% by volume of hydrogen will then circulate in the second stream 21, and a third gas containing at least approximately 60% by weight of a hydrocarbon charge with a mean weight content of hydrogen element of at least approximately 18% will circulate in the outer third stream 23.

If, however, a mixture of hydrogen and of hydrocarbon charge circulates in this third stream, this "premixed" compound will preferably have a quantity by volume of hydrogen of between 1 and 3 times the quantity by volume of hydrocarbon charge, this ratio being advantageously of the order of 2.

In FIG. 2, the igniting device 5, already shown, allows a diffusion flame to be ignited between the chlorine and the hydrogen which are present in the first and second gases.

The products of this diffusion flame then mix with the third gas, rich in hydrocarbons which surround these products, thus triggering the conversion reaction of the hydrocarbon charge.

Finally, the conversion products and more generally the effluents are recovered in the recovery conduits 25, in this case situated at the base of the chamber 7, optionally after quenching.

As in the version of FIG. 1, it may turn out to be advantageous to make the outer walls 7a of this chamber 7 of a thermally conductive material and to provide this same chamber with a wetted surface/volume ratio of between approximately 40 and 250 $m^{-1}$ to make it possible to carry out simultaneously indirect quenching of the effluents and a preheating of all or part of the reactants in the preheating chambers 15 which in this case extend in contact with and along the said walls 7a between, at the top, the height where the gases are ignited and where the conversion reaction is initiated and, at the bottom, the place where the chamber 7 widens, via the divergent part 27.

Additionally, this first "indirect" quenching could be followed by a second, direct quenching conducted, for example, at the outlet of the conduits 25 into a quenching column such as that shown at 11 in FIG. 1 and described above.

In the case of FIG. 2, it will have been noted that this is the typical case of a conversion reactor with a chlorine/hydrogen diffusion flame, the feed streams being in this case interrupted at the entry of the chamber 7 substantially at the same single height.

A stagewise reactant entry, as illustrated in FIG. 3, could, however, be preferred.

In this FIG. 3, three substantially "concentric" and parallel streams 31, 33 and 35 have been provided and are fed, from the interior towards the exterior of the reactor, essentially with chlorine, hydrogen and hydrocarbon charge respectively.

The first central chlorine feed conduit 31 is interrupted first, thus defining a first reaction chamber 37 bounded approximately downstream by the interruption of the second conduit 33 which feeds hydrogen and which surrounds the first. The igniting device 39 situated in the chamber 37 allows a diffusion flame to be ignited between the chlorine-rich first gas and the hydrogen-rich second gas.

On leaving the chamber 37, the products of the diffusion flame receive around them the third gas containing the hydrocarbon charge to be converted, which emerges from the outermost conduit 35, in this case just upstream of the entry of the chamber 7, bounded here by its entry neck 7b.

To illustrate the invention, two examples will now be given, no limitation being implied.

EXAMPLE 1

The reactor employed is of the type illustrated in FIG. 1.

The conduit 1 is fed with chlorine, the conduit 2 with hydrogen and the conduit 6 with methane preheated to approximately 500° C. after passing through the preheating chambers 15. The three gases are in volume proportions of 1/0.8/1 respectively. At the exit of the conduit 4, the ignition is initiated by the device 5 and the conversion reaction takes place in the reaction chamber 7. The pressure in the reactor is slightly higher than atmospheric pressure. The gas mixture collected via the conduit 8 contains essentially unreacted mixture, ethane, ethylene, acetylene, hydrogen and hydrochloric acid, and even perhaps benzene.

EXAMPLE 2

The reactor employed is of the type shown diagrammatically in FIG. 2.

The conduit 19 is fed with chlorine, the conduit 21 with hydrogen and the conduit 23 with a natural gas containing approximately 76% of methane by volume, 12% of ethane, 8% of propane, 2% of butanes and small quantities of various organic and inorganic gases. The chlorine, the hydrogen and the natural gas are in volume proportions of 0.9/0.8/1 respectively. The natural gas has been preheated to approximately 500° C. After conducting the reaction at a pressure close to atmospheric, the gases originating from the conduit 25 are collected. The collected mixture contains essentially methane, ethane, ethylene, propene, hydrogen and hydrochloric acid, as well as acetylene, propane, butanes, butenes and butadiene.

I claim:

1. A method for converting saturated hydrocarbon(s) having a mean weight content of hydrogen element of at least substantially 18% into unsaturated hydrocarbon(s), which comprises reacting by ignition:
   a mixture of a first gas containing at least substantially 30% by volume of chlorine and a second gas containing at least substantially 30% by volume of hydrogen,
   with a third gas surrounding said mixture of said first and second gas and containing at least substantially 60% by weight of a saturated hydrocarbon(s) charge having a mean weight content of hydrogen element of at least substantially 18% to essentially form, as resulting products, hydrogen, hydrochloric acid and unsaturated hydrocarbons containing at least one member selected from the group consisting of acetylene, ethylene, propylene, butene, butadiene, and mixtures thereof.

2. A method according to claim 1 wherein said saturated hydrocarbons to be converted are selected from the group consisting of methane, ethane, propane and mixtures of alkanes having a mean weight content of hydrogen element of at least substantially 18%.

3. A method according to claim 1 wherein said reaction proceeds under conditions to provide an hydrocarbon conversion temperature between 700° and 1,600° C.

4. A method according to claim 1 wherein said reaction is carried out under a pressure between $0.5 \times 10^5$ Pa and $50 \times 10^5$ Pa.

5. A method according to claim 1 wherein the quantity by volume of chlorine present in the first gas is lower than or equal to the quantity by volume of alkanes present in the third gas.

6. A method according to claim 1 wherein the quantity by volume of hydrogen present in the second gas is at least equal to a half of the quantity by volume of chlorine present in the first gas.

7. A method according to claim 1 which further includes the steps of quenching said resulting products, reforming chlorine from said hydrochloric acid, and recycling said reformed chlorine to constitute, at least partially, said first gas.

8. A method according to claim 1 which further includes the steps of quenching said resulting products, separating hydrogen from said quenched resulting products and recycling said separated hydrogen to constitute, at least partially, said second gas.

9. A method according to claim 1 which further includes the steps of quenching said resulting products, separating the alkanes from said quenched resulting products and recycling said separated alkanes to constitute, at least partially, said third gas.

10. A method according to claim 1 which further includes the step of preheating said third gas up to substantially 500° C. before reacting it by ignition with said mixture of said first and second gases.

11. A method for converting saturated hydrocarbon(s) having a mean weight content of hydrogen element of at least substantially 18% into unsaturated hydrogen(s), which comprises:
    mixing a first gas containing at least substantially 30% by volume of chlorine and a second gas containing at least substantially 30% by volume of hydrogen,
    circulating, around said mixture, a third gas containing at least substantially 60% by weight of a saturated hydrocarbon(s) charge having a mean weight content of hydrogen element of at least substantially 18%, without mixing therebetween, and
    in a predetermined zone of circulation, igniting said mixture of said first and second gases, and mixing said ignited mixture with said third gas, to provide reaction therebetween for essentially forming, as resulting products, hydrogen, hydrochloric acid, and unsaturated hydrocarbons containing at least one member selected from the group consisting of acetylene, ethylene, propylene, butene, butadiene, and mixtures thereof.

12. The method according to claim 11 wherein said saturated hydrocarbons to be converted are selected from the group consisting of methane, ethane, propane, and mixtures of alkanes having a mean weight content of hydrogen element of at least substantially 18%.

13. A method for converting saturated hydrocarbon(s) having a mean weight content of hydrogen element of at least substantially 18% into unsaturated hydrocarbon(s), which comprises:
    a) providing, as starting substances, a first gas containing at least substantially 30% by volume of chlorine, a second gas containing at least substantially 30% by volume of hydrogen, and a third gas containing at least substantially 60% by weight of a saturated hydrocarbon(s) charge with a mean weight content of hydrogen element of at least substantially 18%,
    b) circulating these substances independently of each other, without mixing, while said third gas circulates around said first and second gases, and
    c) in a circulation zone, allowing said first and second gases to mix, igniting the mixture thereof and allowing said ignited mixture to mix with said third gas, so as to induce conversion reactions for essentially forming, as resulting products, hydrogen, hydrochloric acid, and unsaturated hydrocarbons containing at least one member selected from the group consisting of acetylene, ethylene, propylene, butene, butadiene, and mixtures thereof.

14. A method according to claim 13 wherein said saturated hydrocarbons to be converted are selected from the group consisting of methane, ethane, propane, and mixtures of alkanes having a mean weight content of hydrogen element of at least substantially 18%.

15. A method according to claim 13 wherein during step b) said first gas is circulated in the center surrounded by said second gas, itself surrounded by said third gas.

* * * * *